United States Patent
Klein

(10) Patent No.: US 6,630,134 B1
(45) Date of Patent: Oct. 7, 2003

(54) GUERBET WAX ESTERS IN PERSONAL CARE APPLICATIONS

(75) Inventor: Kenneth Klein, Fair Lawn, NJ (US)

(73) Assignee: Zenitech LLC, Old Greenwich, CT (US)

( * ) Notice: Subject to any disclaimer, the term of this patent is extended or adjusted under 35 U.S.C. 154(b) by 0 days.

(21) Appl. No.: 10/039,978

(22) Filed: Jan. 8, 2002

(51) Int. Cl.[7] .............................. A61K 7/06; A61K 7/48
(52) U.S. Cl. ..................... 424/70.1; 424/64; 424/401
(58) Field of Search .............................. 424/70.1, 401, 424/64

(56) References Cited

U.S. PATENT DOCUMENTS

| | | | |
|---|---|---|---|
| 4,830,769 A | | 5/1989 | O'Lenick |
| 5,736,571 A | * | 4/1998 | O'Lenick, Jr. .............. 514/549 |
| 5,786,389 A | * | 7/1998 | O'Lenick et al. ........... 514/552 |

* cited by examiner

*Primary Examiner*—Jyothsna Venkat

(57) ABSTRACT

The present invention relates to the cosmetic use of certain reconstituted wax esters, prepared by the reaction of a guerbet alcohol and a natural high molecular wax ester selected from the group consisting of beeswax, candelillia, and carnauba wax. These materials are useful in making waxes with specific melting points and degrees of hardness for personal care applications like lipsticks, and a variety of other applications personal care formulations. The waxes provide conditioning effects when applied to the hair and skin.

5 Claims, No Drawings

GUERBET WAX ESTERS IN PERSONAL CARE APPLICATIONS

TECHNICAL FIELD

The present invention relates to use of certain guerbet wax esters, prepared by the reaction of a guerbet alcohol and a natural high molecular wax ester selected from the group consisting of beeswax, candelillia, and carnauba wax in personal care applications. These materials are useful in preparation of cosmetic products where their ability to make custom chosen melting point waxes, and custom chosen softness of a wax for particular applications is desired. One major area for the use of these materials is in lipsticks and skin cremes where the melting point effects skin spreadability.

BACKGROUND OF THE INVENTION

The present invention relates to compositions that result from the transesterification of a wax ester and any compound that is a guerbet alcohol. Waxy esters derived from the reaction of a fatty acid and hydroxy silicone are known. U.S. Pat. No. 5,180,843 to O'Lenick, (January 1992) teaches that fatty acids, and triglycerides can be reacted with hydroxy containing silicone compounds to form esters. The products of the referenced O'Lenick patent are different in several regards than the compounds of the present invention.

Specifically, the O'Lenick patented products are made from silicone. The by-product of such a reaction is water, glycerin, or methanol respectively. As will become clear from reading the disclosure of the present invention, the compounds of the present invention are made by reacting a specific type wax ester which has a long chain acyl moiety, and a long chain alcohol moiety in the ester. The reaction of such a material with a guerbet alcohol is indicated by the following reaction:

$R^1$—C(O)—O$R^2$+$R^3$—OH→$R^1$—C(O)—O—$R^2$+$R^2$OH.

We have surprisingly found that the guerbet branched ester in presence of the $R^2$OH in the reaction mixture, results in enhanced solubility, compatibility and gives a product with altered melting point and skin feel.

OBJECT OF THE INVENTION

It is the object of the present invention to provide unique cosmetic compositions that can be made to a variety of melting points and hardness for specific applications. These waxy materials are applied to the skin and hair to provide softening and conditioning effects. These materials are applied to the skin and hair in an effective conditioning concentration. The concentration ranges from 0.1% to 85% by weight of the cosmetic product.

DETAILED DESCRIPTION OF THE INVENTION

Beeswax, carnauba wax and candelilla wax contain natural esters, which conform to the following structure:

$R^1C(O)O$—$R^2$ wherein:
$R^1$ is alkyl having 19 to 37 carbon atoms,
$R^2$ is alkyl having 20 to 38 carbon atoms.
The relatively high number of carbon atoms in the compounds is one factor that makes these waxes somewhat unique, compared to oils like tallow, coconut oil, and soybean oil. This higher molecular weight and the fact that it causes the product to be solid, and quite hard. This hardness limits the area into which the waxes can be placed. Reaction with guerbet alcohols results in softer waxes that are more aestethically appealing on the skin. This invention relates to a particular group of highly branched esters made by the reaction of a guerbet alcohol and a wax.

Guerbet Alcohols

Guerbet Alcohols are regiospecifically beta branched alcohols. They have been known since the 1890's when Marcel Guerbet first synthesized them. (M. Guerbet, C. R. Acad. Sci. Paris, 128, 511; 1002 (1899)). These materials are high in molecular weight and are liquid to very low temperatures. The guerbet reaction gives very specific branching in the alcohol as shown;

As can be seen by the above reaction the molecules have substitution on the second carbon from the hydroxyl group. This branching has been found to be critical to the preparation of a product having the desired lubrication and oxidative stability properties. If the branching were on the same carbon as the hydroxyl group, the hydroxyl group would be a secondary one and would be very hindered and has low reactivity. As one moves the branch position away from the beta carbon, the liquidity, lubricity and metal substantivity decreases. If the branch is lower alkyl like methyl in some oxo alcohols, there is little increase in the liquidity, lubricity and metal substantivity over normal alcohols having the same number of carbons. Additionally, the oxo process gives only some beta branching (between 1 and 28%) the guerbet process gives essentially 100% product. Guerbet alcohols that are the reaction product of one specific raw material alcohol will result in a so-called "homo-guerbet". In this case R and R' are identical. If the starting alcohols used in the guerbet reaction are of differing molecular weights a so-called "hetero-guerbet" results. This type of guerbet has a mixed distribution of all possible combinations of alcohols. For this reason R and R' in the generic formula may be the same or different.

Heteroguerbet

Homoguerbet

Guerbet alcohols are available commercially from Sassol Corporation, formerly called Condea Vista.
Guerbet alcohols conform to the following structure:

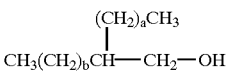

Wherein;
a in an integer ranging from 3 to 11;
b in an integer ranging from 5 to 19.

It should be clear from the reaction sequence that the Guerbet alcohol is reacted into the ester, making a new-branched ester and leaving a free alkyl alcohol (the R²OH), reacted from the starting wax. The resulting composition contains a branched ester and an alcohol that is derived from the original wax. The selection of the guerbet and wax determines the melting point and the degree of hardness of the wax. This is very important in a variety of applications, like automotive polishes, and personal care products like lipsticks.

The compositions of the present invention when applied to the hair and skin and provide softening and conditioning effects and have a soothing feel on the skin. The present invention relates to a process for conditioning hair and skin, which comprises contacting the hair or skin with an effective conditioning concentration of a composition which comprises:

a) An ester conforming to the following structure:

$R^1$ is alkyl having 19 to 37 carbon atoms,
$R^3$ is:

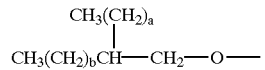

a in an integer ranging from 3 to 11;
b in an integer ranging from 5 to 19.

b) a hydroxy compound conforming to the following structure:

wherein;
$R^2$ is alkyl having 20 to 38 carbon atoms.

In a preferred embodiment the concentration of the hydroxy compound ranges from 1 to 10% by weight.

In another preferred embodiment the concentration of the hydroxy compound ranges from 5 to 10% by weight.

In another preferred embodiment a is an integer ranging from 3 to 11.

In another preferred embodiment b is an integer ranging from 5 to 19.

In a preferred embodiment a is 3 b is 5.
In a preferred embodiment a is 5 b is 7.
In a preferred embodiment a is 7 b is 9.
In a preferred embodiment a is 9 b is 11.
In a preferred embodiment a is 13 b is 15.
In a preferred embodiment a is 15 b is 17.
In a preferred embodiment a is 11 b is 19.

In a preferred embodiment the concentration ranges from 0.1% to 85% by weight of the cosmetic product.

The products are applied to the skin or skin by rubbing. The products may be used as is or formulated into an emulsion with a surfactant and water using emulsification techniques known to those skilled in the art. Vitamins, fragrances, sunscreens and the like can also be added.

Waxes

The waxes useful as raw materials in the preparation of the compositions of the present invention are commercially available Koster Kuennen Corporation.

Beeswax

Beeswax, which is also known as white wax, is an insect wax cultured worldwide; it is found on all continents of the globe. The chemical composition of the wax varies slightly depending upon the specie of the bee producing the wax. To extract the beeswax for use the honeycomb is melted or boiled with water and the crude wax is skimmed off the top. The color of the crude material is dependent upon the type of flower producing the pollen and the age of the hive. Natural waxes of animal origin are complex in structure and as such, possess unique properties that render then invaluable raw material for many of today's industries.

Natural Beeswax is amorphid and varies in color from a deep brown to a light taffy shade. The wax has a distinctive honey odor. Beeswax has a melting point of between 62–65° C. Beeswax has CAS number of #8006-40-4.

Carnauba Wax

Currently, the only place in the world where the Carnauba Palm tree can be found is in northeastern Brazil. This Palm tree (*Capernicea cerifera*), often called the "tree of life," produces a wax on its leaves, protecting them from the severe weather conditions of the area. Harvesting occurs around September following traditional procedures, the leaves are cut and are laid on the ground to dry in the sun. Modern technology takes over to scrape this valued product from its leaf. Two types of wax are obtained, one pure and clear from the center of unopened leaves, called yellow grade wax; the second from the leaf itself called gray powder.

Carnauba Wax is an environmentally correct natural raw material and is the hardest of the natural waxes. In addition, it has the highest melting point of waxes and is brittle and nontacky. Carnauba possesses excellent gelling properties, is emulsifiable and also has the ability of retaining oil. These properties assure its premiere position in the global market place, for food, pharmaceutical, and advanced technologies.

Carnauba, beeswax and candellillia wax are soluble in vegetable and animal waxes and a large variety of natural and synthetic resins as well as fatty acids, glycerides, and hydrocarbons.

Guerbet Examples

| Example | Designation | a | b |
|---------|-------------|----|----|
| 1 | Guerbet C12 | 3 | 5 |
| 2 | Guerbet C16 | 5 | 7 |
| 3 | Guerbet C20 | 7 | 9 |
| 4 | Guerbet C24 | 9 | 11 |
| 5 | Guerbet C28 | 11 | 13 |
| 6 | Guerbet C32 | 13 | 15 |
| 7 | Guerbet C36 | 15 | 17 |
| 8 | Guerbet C40 | 17 | 19 |

EXAMPLE WAXES

Example 9 is beeswax,
Example 10 is candelillia wax
Example 11 is carnauba wax

General Procedure

The compounds of the present invention are prepared by the transesterification reaction of the wax and the guerbet alcohol. The reaction is carried out with a molar ratio of 0.5:1 wax to guerbet to 1:0.5 ratio with a preferred mole ratio of 1:1. The wax and the polymer are added to a suitable reaction vessel under agitation. The two are heated to 160–250 C. with a preferred temperature of between 180–200 C. An esterification catalyst selected from para toluene sulfonic acid, tin oxylate, sulfuric acid and other esterification catalysts. The reaction is conducted at 180 to 200 C. for three to eight hours. During that time alkyl alcohol is generated. This alcohol has found to be a critical element to the composition's functionality. Its presence allows for better coupling of the product when put in formulations. Specifically, the alcohol, and the guerbet ester together make up a coupling composition that allows for the compatabilization of oil phases and silicone phases that are normally incompatible.

Example 12

To 2914.3 grams of guerbet alcohol (example 1) is added 606.8 grams of the specified wax (example 9). Next is added 0.1% by weight, based upon the total number of grams of total reaction mass of tin oxylate. The reaction mass is heated to 200 C., and held for 3–6 hours. The resulting composition is used as prepared without additional purification.

Example 13–110

Example 13 is repeated, only this time the specified amount of the specified silicone polymer replaces the prior silicone polymer and the specified wax and quantity of wax replaces the wax specified in Example 12.

| | Guerbet Alcohol | | Wax | |
|---|---|---|---|---|
| Example | Example | Grams | Example | Grams |
| 13 | 1 | 100.0 | 9 | 100.0 |
| 14 | 2 | 12540.0 | 9 | 1254.0 |
| 15 | 3 | 9017.0 | 9 | 3526.0 |
| 16 | 4 | 3082.2 | 9 | 1340.0 |
| 17 | 5 | 100.0 | 9 | 1236.7 |
| 18 | 6 | 1574.0 | 9 | 300.8 |
| 19 | 7 | 2636.7 | 9 | 500.7 |
| 20 | 8 | 1580.6 | 9 | 1580.0 |
| 21 | 1 | 3306.2 | 10 | 690.0 |
| 22 | 2 | 1449.1 | 10 | 750.9 |
| 23 | 3 | 554.0 | 10 | 500.0 |
| 24 | 4 | 1789.2 | 10 | 400.8 |
| 25 | 5 | 3067.1 | 10 | 667.9 |
| 26 | 6 | 2205.8 | 10 | 689.0 |
| 27 | 7 | 578.0 | 10 | 120.0 |
| 28 | 8 | 5206.9 | 10 | 520.6 |
| 29 | 8 | 22898.0 | 10 | 2289.8 |
| 30 | 1 | 6203.9 | 11 | 3101.5 |
| 31 | 2 | 9119.1 | 11 | 911.9 |
| 32 | 3 | 1735.4 | 11 | 357.9 |
| 33 | 4 | 6288.0 | 11 | 928.8 |
| 34 | 5 | 3344.1 | 11 | 668.5 |
| 35 | 6 | 2750.1 | 11 | 600.8 |

Carnauba Wax is a hard, brittle, non-tacky and lustrous wax, having a melting point of between 83.0–86 C. It's CAS number is 8015-86-9.

Candelillia Wax

Candelillia Wax is extracted from the outer surface of Candelilla plants, which are native to the arid regions of Northern Mexico. The plants grow wild in the plains and in the foothills of Mexico's North-Central plateau. With a melting point ranging from 66 to 71 C., candellillia is well suited to the preparation of many wax products where resistance to heat is an important consideration. Candelilla wax is used in polishes dressings, coatings, and finishes, where a reasonably high melting point is desirable. In addition, this wax blends easily with fatty acids, paraffin, and other waxes used in the manufacture of candles and tapers. Candellillia can be used for dyes in the printing of various materials providing excellent lubricant properties and resistance to high pressure.

Candelillia is a light brown to light yellow, hard, brittle, slightly tack and lustrous wax with a distinctive odor. This wax is not as hard as Carnauba and does not reach its maximum hardness until several days after cooling. It has a melting point of between 68.5–72.5

| | Guerbet Alcohol | | Wax | |
|---|---|---|---|---|
| Example | Example | Grams | Example | Grams |
| 36 | 7 | 4483.1 | 11 | 897.9 |
| 37 | 8 | 5207.9 | 11 | 520.8 |
| 38 | 9 | 2914.2 | 11 | 600.9 |
| 39 | 3 | 900.0 | 9 | 100.0 |
| 40 | 3 | 400.0 | 9 | 100.0 |
| 41 | 3 | 400.0 | 9 | 400.0 |
| 42 | 3 | 600.0 | 9 | 400.0 |
| 43 | 3 | 700.0 | 9 | 300.0 |
| 44 | 3 | 750.0 | 9 | 250.0 |
| 45 | 3 | 800.0 | 9 | 200.0 |

Applications Examples

The compounds of the present invention, unlike the beeswax from which they are derived are soft waxes that can be prepared at a specific melting point. The ability to make a product that melts near body temperature has resulted in a butter rather than a wax. We refer to that product as beesbutter. The technology is applicable to making waxes with specific melting points and degrees of hardness for personal care applications like lipsticks, polish and a variety of other applications.

Typical of the way in which the melting point can be modified is using beeswax.

| Material | Melt Point ° C. | Appearance |
|---|---|---|
| Beeswax | 62 | Hard Wax |
| Example 39 | 58 | Wax |
| Example 40 | 50 | Soft wax |
| Example 41 | 48 | Soft wax |
| Example 42 | 42 | Soft wax |
| Example 43 | 40 | Stiff butter |
| Example 44 | 37 | Butter |
| Example 45 | 35 | Soft butter |

Typical of formulations using the compounds of the present invention are:

Emollient Lipstick

| NO. | INGREDIENT | % Weight |
|---|---|---|
| 1 | Pale Pressed Castor Oil | 23.1 |
| 2 | Candelilla | 7.0 |
| 3 | Carnuba No. 1 Flakes | 2.1 |
| 4 | Ozokerite | 2.0 |
| 5 | Microcrystalline Wax | 3.5 |
| 6 | Example 15 | 15.0 |

-continued

| NO. | INGREDIENT | % Weight |
|---|---|---|
| 7 | Isostearyl Stearoyl Stearate | 15.0 |
| 8 | Octyl dodecanol | 6.0 |
| 9 | Hydrogenated Lanolin, | 1.0 |
| 10 | Glycerl Triisostearate | 9.5 |
| 11 | Methyl Paraben | 0.2 |
| 12 | Propyl Paraben | 0.1 |
| 13 | 35% D&C Red #7 Castor Oil | 5.5 |
| 14 | 30% FD&C Blue #1 AI Lake/Castor Oil | 2.0 |
| 15 | 40% Red Iron Oxide/Castor Oil | 4.0 |
| 16 | Sil Mica | 4.0 |

Premill pigment grinds using a three roll mill. Combine waxes, oils, and preservatives. Heat to 85° C. with propellor agitation until clear. Adjust temperature to 75–80° C. Add pigment grinds and mica, stirring until homogeneous. Fill into molds at 70° C.

The presence of Example 15 in the formula provides emmoliency and conditioning to the skin.

| | % Weight |
|---|---|
| PHASE A | |
| Petroleum Jelly | 84.2 |
| Example 15 | 3.0 |
| Castor isosterarate succinate | 3.0 |
| PHASE B | |
| Castor Oil | 9.0 |
| PHASE C | |
| Vitamin E Acetate | 0.1 |
| Germaben IIe | 0.5 |
| Fragrance | 0.2 |

Manufacturing Instructions:

1. Heat Phase A to 65° C.
2. Add Phase B, mixing to uniformity after each addition.
3. At 45° C. add Phase C, stirring well after each addition. Package.

The presence of Example 15 in the formula provides emmoliency and conditioning to the hair.

What is claimed is:

1. A process for conditioning hair and skin, which comprises contacting the hair or skin with an effective conditioning concentration of a composition made by the esterification reaction of a guerbet alcohol conforming to the following structure:

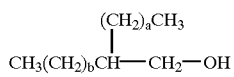

wherein a in an integer ranging from 3 to 11;

b in an integer ranging from 5 to 19;

with a wax selected from the group consisting of beeswax, carnauba and candelillia wax wherein said esterification reaction is carried out at a temperature of between 180° C. and 200° C.

2. A process of claim 1 wherein said wax is beeswax.

3. A process of claim 1 wherein said wax is carnauba.

4. A process of claim 2 wherein said wax is candelillia wax.

5. A process of claim 2 wherein said effective conditioning concentration ranges from 25% to 0.1% by weight.

* * * * *

UNITED STATES PATENT AND TRADEMARK OFFICE
CERTIFICATE OF CORRECTION

PATENT NO. : 6,630,134 B1
DATED : October 7, 2003
INVENTOR(S) : Klein, Kenneth

It is certified that error appears in the above-identified patent and that said Letters Patent is hereby corrected as shown below:

Column 4,
Lines 25 and 26, change "silicone polymer" and insert therefore -- Guerbet compound --

Column 5,
Line 24, change "Example 13-110" and insert therefore -- Example 13- 45 --

Signed and Sealed this

Twenty-third Day of December, 2003

JAMES E. ROGAN
*Director of the United States Patent and Trademark Office*